United States Patent
Cedars et al.

(10) Patent No.: US 12,245,792 B2
(45) Date of Patent: Mar. 11, 2025

(54) CERVICAL CERCLAGE WITH SURGICAL BUTTONS

(71) Applicants: Leonard Cedars, Dallas, TX (US); Roman Starikov, San Diego, CA (US)

(72) Inventors: Leonard Cedars, Dallas, TX (US); Roman Starikov, San Diego, CA (US)

( * ) Notice: Subject to any disclaimer, the term of this patent is extended or adjusted under 35 U.S.C. 154(b) by 890 days.

(21) Appl. No.: 17/001,521

(22) Filed: Aug. 24, 2020

(65) Prior Publication Data
US 2022/0054170 A1    Feb. 24, 2022

(51) Int. Cl.
| A61B 17/42 | (2006.01) |
| A61B 17/04 | (2006.01) |
| A61B 17/00 | (2006.01) |
| A61B 17/11 | (2006.01) |
| A61B 90/00 | (2016.01) |

(52) U.S. Cl.
CPC ...... *A61B 17/4241* (2013.01); *A61B 17/0401* (2013.01); *A61B 2017/00893* (2013.01); *A61B 2017/0414* (2013.01); *A61B 2017/1142* (2013.01); *A61B 2017/4225* (2013.01); *A61B 2090/3966* (2016.02)

(58) Field of Classification Search
CPC ...... A61B 17/0401; A61B 2017/00893; A61B 2017/0414; A61B 2017/1142; A61B 2017/4225; A61B 2017/0404; A61B 17/0483; A61B 17/42; A61M 31/002
See application file for complete search history.

(56) References Cited

U.S. PATENT DOCUMENTS

| 3,840,005 | A * | 10/1974 | Walker | A61F 6/144 219/121.84 |
| 5,273,054 | A * | 12/1993 | Walker | A61F 6/148 128/830 |
| 8,551,139 | B2 * | 10/2013 | Surti | A61B 17/0401 606/232 |
| 9,339,362 | B2 * | 5/2016 | Goldberg | A61B 17/4241 |
| 9,486,431 | B2 * | 11/2016 | McClain | A61K 31/715 |
| 10,390,816 | B2 * | 8/2019 | Thornes | A61B 17/068 |
| 11,304,691 | B2 * | 4/2022 | Epstein | A61B 17/0401 |
| 2005/0261547 | A1 * | 11/2005 | Bouffier | A61B 17/0401 128/DIG. 25 |
| 2013/0066145 | A1 * | 3/2013 | Fairneny | A61F 2/0045 600/37 |

* cited by examiner

*Primary Examiner* — Julian W Woo

(57) ABSTRACT

Embodiments of the present invention provide a cervical cerclage apparatus and a method for performing a cervical cerclage. In an embodiment of the invention, a cervical cerclage apparatus includes, a length of suture and at least two stitched regions formed by the length of suture around an exterior surface of a cervix. The cervical cerclage apparatus further includes at least two surgical buttons attached the length of suture, each surgical button comprising an inner face and an outer face, wherein the inner face of each surgical button are configured to be placed against the exterior surface of the cervix between the stitched regions, wherein at least one of the surgical buttons comprises Progesterone.

5 Claims, 3 Drawing Sheets

CERVICAL CERCLAGE WITH SURGICAL BUTTONS

BACKGROUND OF THE INVENTION

Field of the Invention

The present invention relates to the field of cervical medical procedures and more particularly to cervical cerclages.

Description of the Related Art

The preterm birth rate in the United States in 2016 was approximately 9.6% and about one third or 36% of infant deaths were due to prematurity-related causes. As well, preterm birth is a leading cause of long-term neurological disabilities in children. Cervical insufficiency, a known cause contributing to prematurity and its sequela, is believed to be present in up to 1% of obstetric populations. While the definition of cervical insufficiency has been debated, the American College of Obstetricians and Gynecologists defines it as the inability of the uterine cervix to retain a pregnancy in the absence of the signs and symptoms of clinical contractions, or labor, or both in the second trimester. Classically, cervical insufficiency is described as painless, progressive dilatation of the uterine cervix resulting in membrane prolapse, premature rupture of the membranes, midtrimester pregnancy loss, or preterm birth.

Current data supports the use of cervical cerclages for certain women at risk for preterm delivery due to cervical insufficiency with the goal to achieve a greater gestational age. Cervical cerclages are associated with significant decreases in preterm birth outcomes, as well as improvements in composite neonatal morbidity and mortality. While the benefits of cervical cerclages are clear, it is important to note that there are significant complications that can occur, including: intra-amniotic infection predisposing to sepsis, premature rupture of membranes, premature labor, cerclage migration, cervical laceration at delivery and hemorrhage.

In addition to cervical cerclages, Progesterone is recommended to decrease the risk of premature delivery in patients. Normally, Progesterone is administered through intramuscular injection for patients with a prior preterm birth or applied intra-vaginally in patients without a history of premature delivery, but who have an incidentally-noted short cervix. For the purpose of this patent application, "Progesterone" means the biologic hormone, progesterone, or any similar hormone with progesterone-like activity (progestin), which is considered safe for use in pregnancy.

Due to the constraints associated with visiting a medical professional for injectable Progesterone, and the inconvenience and potential inconsistency of self-application of vaginal Progesterone, patients may benefit from a controlled drug release delivery system that allows the drug to be released into the human body at desired time intervals and dosages. Controlled drug release delivery systems may take the form of coatings that are broken down through diffusion or biodegradation, reservoirs that release the drug through a porous membrane or combinations of reservoirs and coatings.

BRIEF SUMMARY OF THE INVENTION

Embodiments of the present invention address deficiencies of the art in respect to cervical cerclages and provide a novel and non-obvious apparatus and method for cervical cerclages including Progesterone. In an embodiment of the invention, a cervical cerclage apparatus includes a length of suture and at least two stitched regions formed by the length of suture around an exterior surface of a cervix. The cervical cerclage apparatus further includes at least two surgical buttons attached the length of suture, each surgical button including an inner face and an outer face, wherein the inner face of each surgical button is configured to be placed against the exterior surface of the cervix between the stitched regions, wherein at least one of the surgical buttons comprises Progesterone.

In one aspect of the embodiment, the length of suture secures the inner face of each of the surgical buttons against the exterior surface of the cervix on opposite sides of the cervix. In another aspect of the embodiment, the length of suture further includes distal ends of the length of suture at each opposite end of the length of suture, wherein each distal end includes a portion of the length of suture that are configured to remain proximate to the exterior surface of the cervix. In yet another aspect of the embodiment, each of the distal ends of the length of suture are attached to one of the surgical buttons. In even yet another aspect of the embodiment, each surgical button is attached to the length of suture by threading the suture through at least two holes of the surgical button.

In another aspect of the embodiment, at least one of the surgical buttons includes Progesterone. In yet another aspect of the embodiment, the Progesterone is disposed within a reservoir of the surgical button. In even yet another aspect of the embodiment, the Progesterone is disposed within at least one coating of the surgical button.

In another embodiment of the invention, a method of performing cervical cerclage includes placing a length of suture around an exterior surface of a cervix and attaching at least two surgical buttons along the length of suture, wherein each surgical button includes an inner face and an outer face and wherein at least one of the surgical buttons comprises Progesterone. The method further includes positioning the inner face of each of the surgical buttons against the exterior surface of the cervix and forming at least two stitched regions with the length of suture around the cervix to secure the surgical buttons against the exterior surface of the cervix, wherein the inner face of each surgical button is secured against the exterior surface of the cervix between the stitched regions.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein.

DETAILED DESCRIPTION OF THE INVENTION

Embodiments of the invention provide for an apparatus and method of performing a cervical cerclage by placing a length of suture around a cervix and attaching at least two surgical buttons along the length of suture. The inner face of each of the surgical buttons are placed against the exterior surface of the cervix and at least four purse string stitches are performed using the length of suture around the cervix to secure the surgical buttons against the exterior surface of the cervix between each of the stitched regions of the purse string stitches. In doing so, the surgical buttons disperse the force exerted by the length of suture on the cervix when performing the cervical cerclage. As such, the surgical buttons provide a better occlusion than a single suture or tape and decrease the chance that the suture will cut through the cervical stroma and migrate. Notably, the surgical buttons may include Progesterone, which provides an efficient controlled release delivery system to apply Progesterone intra-vaginally to further decrease the possibility of preterm birth.

Figure 1:
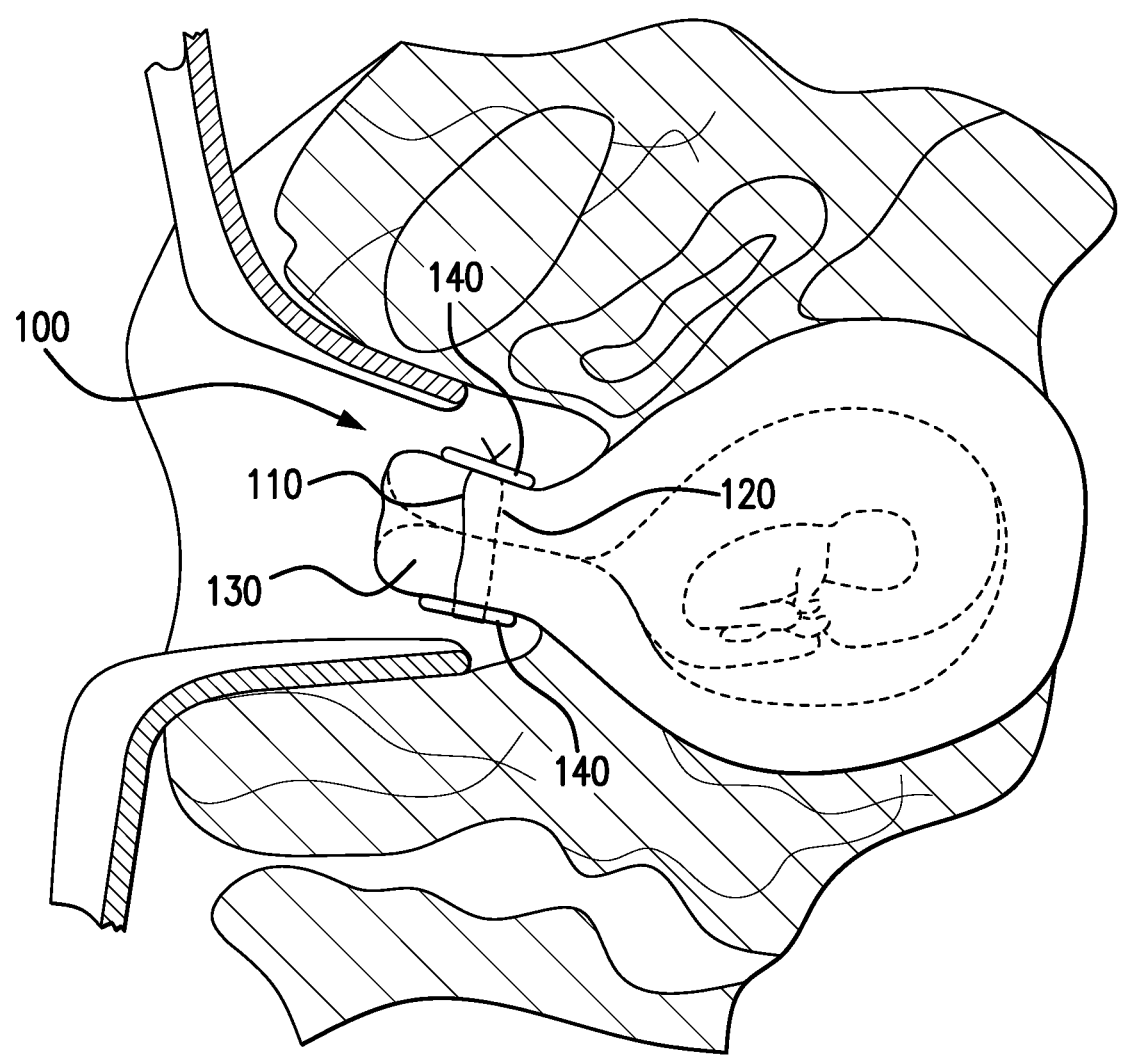
FIG. 1 is a side, cutaway view of a pictorial illustration of a cervical cerclage with surgical buttons in accordance with an embodiment of this invention.
Figure 2:
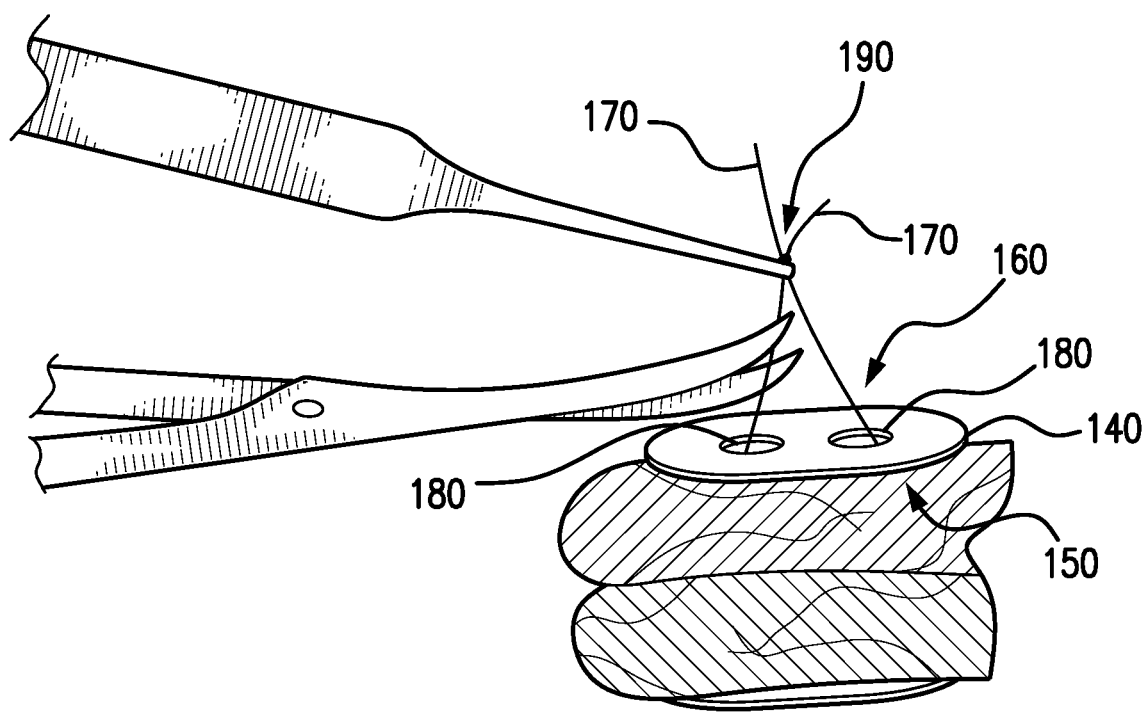
FIG. 2 is a side view of a pictorial illustration for a removal of a cervical cerclage with surgical buttons in accordance with an embodiment of this invention.

In further illustration, FIG. 1 pictorially shows a cervical cerclage with surgical buttons and FIG. 2 pictorially shows removal of a cervical cerclage with surgical buttons in accordance with an embodiment of this invention. As shown in FIGS. 1 and 2 shows a cervical cerclage apparatus that includes a length of suture 110 and at least four stitched regions 120 formed by the length of suture around an exterior surface of a cervix 130. The stitched regions 120 are preferably purse string stitches formed by threading the suture through the exterior surface of the cervix 130. The cervical cerclage apparatus further includes at least two surgical buttons 140 attached the length of suture; each surgical button includes an inner face 150 and an outer face 160. As can be seen, the inner face of each surgical buttons are configured to be placed against the exterior surface of the cervix 130 between the stitched regions 120. As shown in FIG. 2, the length of suture 110 is tightened so that the length of suture secures the inner face 150 of each of the surgical buttons against the exterior surface of the cervix 130 on opposite sides of the cervix between each of the stitched regions 120 to disperse the force of the suture on each of the surgical buttons.

As shown in FIGS. 1 and 2, the length of suture 110 further includes distal ends 170 of the length of suture at each opposite end of the length of suture 110, wherein each distal end 170 includes a portion of the length of suture 110 that are configured to remain proximate to the exterior surface of the cervix 130 and the outer face 160 of the surgical button. Each of the distal ends 170 of the length of suture are attached to one of the surgical buttons 140 by threading the suture through at least two holes 180 of the surgical button 140 and tying a knot 190 with the distal ends 170 above the exterior surface of the cervix and outer face 160 of the button. As can be seen in FIG. 2, the button elevates the knot 190 and helps protect the cervical tissue at the time of removal.

The suture may be of any material used in performing suturing techniques, such as #2 Prolene®. Although preferably the surgical buttons are a flat 19 mm sterile, round, plastic button with two holes, any type of sterile fastener of any shape or size may be used. Preferably, the surgical button or fastener includes a relatively flat surface that is able to disperse the force of the suture along the surgical button or fastener. As well, although two holes are described for the surgical button, any amount of holes in the button that allow for the securing of the button against the cervix may be used. Even further, preferably the buttons are radio opaque, so that the buttons can be identified with medical imaging.

Notably, the surgical buttons or fasteners 140 may include Progesterone and the Progesterone may be disposed within a reservoir of the surgical button or fastener 140, within at least one coating of the surgical button or fastener or any combination of reservoirs and coatings. In doing so, the surgical buttons or fasteners provide an easily applied controlled release delivery system for progesterone in order to apply the Progesterone intra-vaginally. The surgical buttons or fasteners with a controlled release delivery system for Progesterone, used in conjunction with the cervical cerclage, may provide an extremely efficient way to prevent preterm birth.

The suture ends or distal ends 170 at the end of the knot 190 above the button 140 to facilitate identification and removal of the suture 110. Preferably, the suture ends 170 are left 3 to 4 cm long for this reason. Thus, the suture ends 170 at the end of the knot allow for easy removal of the cerclage, as the knot from the suture rests on top of the button 140 anteriorly and can be easily identified even in situations with limited visibility. As well, the button 140 prevents suture migration and protects the suture knot 190 and suture ends 170 from becoming buried in the cervical tissue, especially in situations where there is swelling of the cervix and erosion of the knot into the cervical tissue.

In further illustration of the invention, FIGS. 3A through 4B pictorially show methods of performing cervical cerclages in accordance with embodiments of the invention. The surgical button cerclage technique is routinely performed by the attending physician who is familiar with the technique and a resident physician who often assists and contributes to placement of the cerclage. After administration of spinal anesthesia, the patient is placed in a dorsal lithotomy position. The patient's perineum and outer vagina are prepped in the usual sterile fashion. Following draping, a weighted speculum is placed in the vagina and the cervix is exposed. The cervix is grasped at the six and 12 o'clock positions with a ring forceps and exposed membranes elevated back into the uterus with a glove covered sponge stick, Hagar dilator, or a Foley bulb.

Following the preparation described above, as shown in FIGS. 3A through 4B, a method of performing cervical cerclage includes placing a length of suture 110 around an exterior surface of a cervix 130 and attaching at least two surgical buttons 140 along the length of suture, wherein each surgical button includes an inner face 150 and an outer face 160. The inner face of each of the surgical buttons is positioned against the exterior surface of the cervix 130. At least four stitched regions 120 are formed with the length of suture 110 around the cervix 130 to secure the surgical buttons 140 against the exterior surface of the cervix. As can be seen, the inner face 150 of each surgical button is secured against the exterior surface of the cervix between the stitched regions 120. However, as can be seen from the exemplary embodiments shown in FIGS. 3A through 4B, any number stitched regions 120, preferably formed by purse string stitches, and surgical buttons 140 may be used in performing the cervical cerclage method.

Figure 3A:
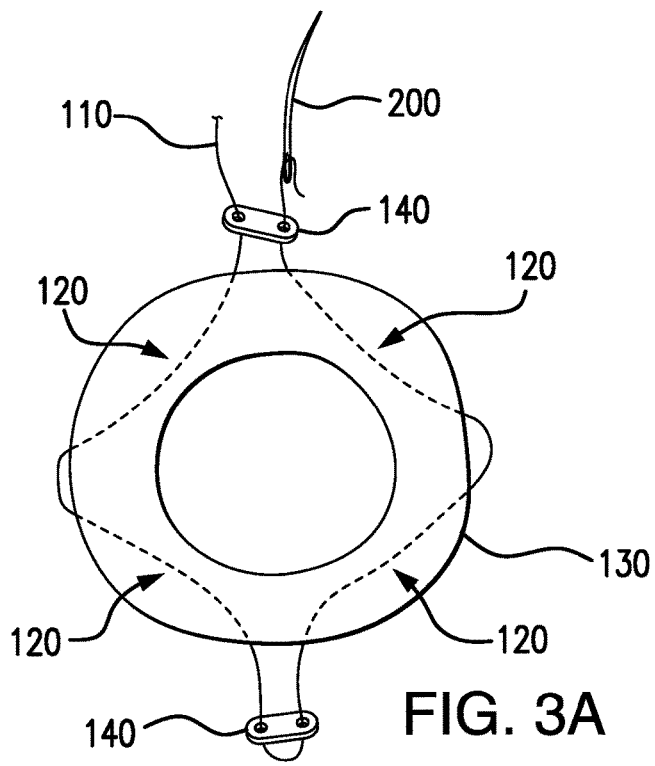
FIGS. 3A and 3B are front views of a pictorial illustration of a method of performing a cervical cerclage with two surgical buttons in accordance with an embodiment of this invention.
Figure 3B:
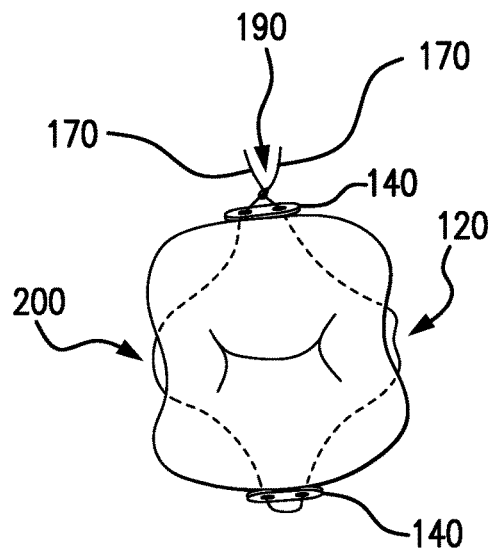

More specifically, FIGS. 3A and 3B pictorially shows a method of performing cervical cerclages in accordance with an embodiment of the invention. As can be seen, after the patient is prepped as discussed above, the method of performing cervical cerclage includes placing a length of suture 110 in a counter-clockwise direction around the cervix 130, starting at the 12 o'clock position of the cervix. The method also includes performing a first purse string stitch by inserting a needle with one of the ends of the length of suture through the exterior surface of the cervix at about the 12 o'clock position of the cervix and exiting the exterior surface of the cervix at about a 10 o'clock position of the cervix to form a first stitched region 120. The method further includes placing a second purse string stitch, inserting the needle at the 8 o'clock position of the cervix and exiting the cervix at the 6 o'clock position of the cervix. At this point, a surgical button 140 is threaded onto the length of suture 110.

The method then includes placing a third purse string suture into the exterior surface of the cervix from about the 6 o'clock position of the cervix to about an 4 o'clock position of the cervix 130. The method then includes placing a fourth purse string stitch by inserting the needle and suture through the exterior surface of the cervix at about the 2 o'clock position of the cervix and exiting the exterior surface of the cervix at about a 12 o'clock position of the cervix. A second surgical button 140 is threaded onto the two distal ends 170 of the length of suture at about the 12 o'clock position of the cervix. The method then includes tightening the length of suture 110 and placing a knot 190 on the external surface of the 12 o'clock button to secure the first and second surgical buttons against the cervix at the 6 o'clock position of the cervix and the 12 o'clock position of the cervix, respectively. Finally, the distal ends 170 of the length of suture are cut to a length that allows for easy identification and removal of the cervical cerclage. Alternatively, these methods may be performed in a clockwise direction, which would be more appropriate for a left-handed surgeon.

Figure 4A:
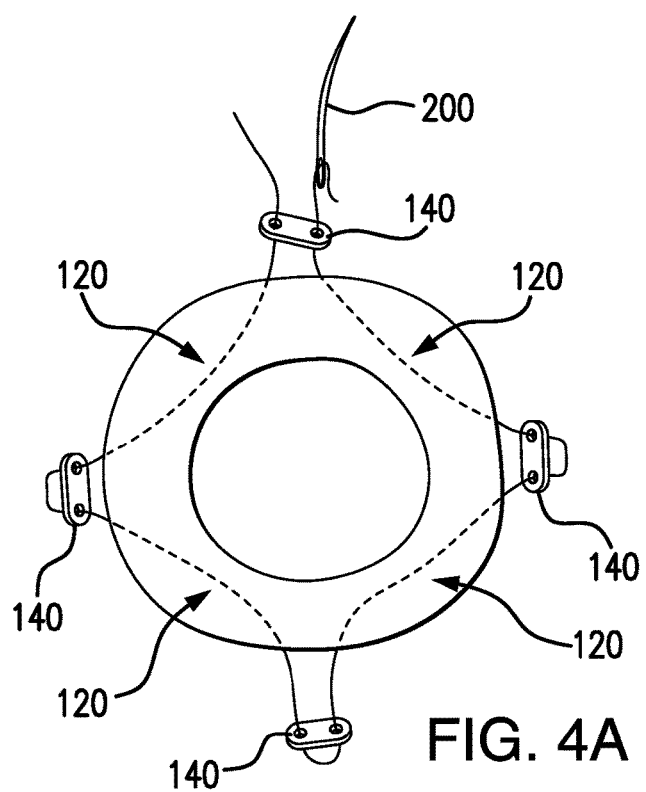
FIGS. 4A and 4B are front views of a pictorial illustration of a method of performing a cervical cerclage with four surgical buttons in accordance with an embodiment of this invention.
Figure 4B:
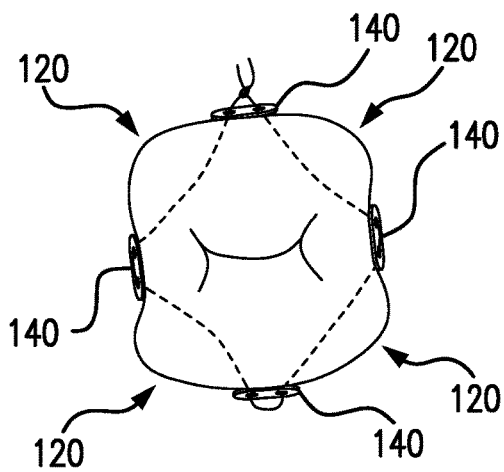

Although FIGS. 3A and 3B shows the above-described specific method of performing the cervical cerclage with buttons, as shown in FIGS. 4A and 4B, any number of stitched regions 120 and surgical buttons 140 may be used in any number of positions around the cervix 130 in order to perform the cervical cerclage method and are within the scope of this invention. The cervical cerclage, that include surgical buttons, provides significant advantages, including prolongation of latency, less cerclage migration, and reduced cervical tissue trauma. Additionally, when the buttons include Progesterone, the cervical cerclage includes the advantages of an efficient controlled release delivery system for Progesterone to further decrease the possibility of pre-term birth.

Although specific embodiments of the invention have been disclosed, those having ordinary skill in the art will understand that changes can be made to the specific embodiments without departing from the spirit and scope of the invention. The scope of the invention is not to be restricted, therefore, to the specific embodiments. Furthermore, it is intended that the appended claims cover any and all such applications, modifications, and embodiments within the scope of the present invention.

Finally, the terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes" and/or "including," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

We claim:

1. A method of performing cervical cerclage, comprising:
   providing a length of suture;
   purse-stitching the length of suture around an exterior surface of a cervix such that at least four stitched regions are formed, the at least four stitched regions including:
      a first stitch through the exterior surface of the cervix between 12 o'clock and 10 o'clock positions of the cervix;
      a second stitch through the exterior surface of the cervix between 8 o'clock and 6 o'clock positions of the cervix;
      a third stitch through the exterior surface of the cervix between 6 o'clock and 4 o'clock positions of the cervix; and
      a fourth stitch through the exterior surface of the cervix between 2 o'clock and 12 o'clock positions of the cervix;
   attaching a first surgical button between the second and third stiches at the 6 o'clock position of the cervix and attaching a second surgical button between the first and fourth stitches at the 12 o'clock position of the cervix such that the second surgical button is opposite the first surgical button, wherein each surgical button defines an aperture and comprises an inner face and an outer face, and wherein at least one of the surgical buttons comprises Progesterone;
   positioning the inner face of each of the surgical buttons against the exterior surface of the cervix; and,
   wherein the at least four stitched regions secure the surgical buttons against the exterior surface of the cervix, wherein the inner face of each surgical button is secured against the exterior surface of the cervix between the stitched regions.

2. The method of performing cervical cerclage of claim 1, wherein the length of suture secures the inner face of each of the surgical buttons against the exterior surface of the cervix on opposite sides of the cervix.

3. The method of performing cervical cerclage of claim 1, wherein each surgical button is attached to the length of suture by threading the suture through at least two apertures of the surgical button.

4. The method of performing cervical cerclage of claim 1, wherein the Progesterone is disposed within a reservoir of the surgical button.

5. The method of performing cervical cerclage of claim 1, wherein the Progesterone is disposed within at least one coating of the surgical button.

* * * * *